United States Patent
Wiggins

(10) Patent No.: US 7,612,560 B2
(45) Date of Patent: Nov. 3, 2009

(54) SELECTIVELY ADJUSTABLE PHANTOM THAT IS COMPATIBLE WITH A MAGNETIC RESONANCE IMAGING SYSTEM AND ENVIRONMENT

(75) Inventor: Christopher John Wiggins, Lynn, MA (US)

(73) Assignee: The General Hospital Corporation, Boston, MA (US)

( * ) Notice: Subject to any disclaimer, the term of this patent is extended or adjusted under 35 U.S.C. 154(b) by 183 days.

(21) Appl. No.: 11/789,242

(22) Filed: Apr. 24, 2007

(65) Prior Publication Data

US 2008/0265882 A1   Oct. 30, 2008

(51) Int. Cl.
   G01V 3/00      (2006.01)
   A61B 5/055     (2006.01)
(52) U.S. Cl. .................. 324/308; 324/321; 600/411
(58) Field of Classification Search ......... 324/300–322; 600/407–435; 250/252.1, 505.1; 378/18, 378/207

See application file for complete search history.

(56) References Cited

U.S. PATENT DOCUMENTS

| | | | | |
|---|---|---|---|---|
| 4,818,943 A | * | 4/1989 | Chandra | 324/318 |
| 5,036,280 A | * | 7/1991 | Chesavage | 324/308 |
| 6,205,871 B1 | | 3/2001 | Saloner et al. | |
| 6,720,766 B2 | | 4/2004 | Parker et al. | |
| 6,822,454 B2 | * | 11/2004 | Peck et al. | 324/321 |
| 7,141,978 B2 | * | 11/2006 | Peck et al. | 324/321 |
| 7,439,493 B2 | * | 10/2008 | Teppaz et al. | 250/252.1 |
| 2002/0149369 A1 | * | 10/2002 | Peck et al. | 324/321 |
| 2003/0086535 A1 | | 5/2003 | Teppaz et al. | |
| 2005/0253587 A1 | * | 11/2005 | Peck et al. | 324/321 |
| 2006/0195030 A1 | | 8/2006 | Ogrezeanu et al. | |
| 2008/0265882 A1 | * | 10/2008 | Wiggins | 324/308 |

* cited by examiner

Primary Examiner—Brij B. Shrivastav
Assistant Examiner—Tiffany A Fetzner
(74) Attorney, Agent, or Firm—Quarles & Brady LLP

(57) ABSTRACT

A phantom for use in an MRI or MRS system includes an array of subresolvable compartments that are each connected to receive fluid from one of a plurality of fluid reservoirs. The array of compartments is divided into sub-arrays which differ from each other by the mix of compartments in each sub-array receiving fluids from the different reservoirs. Studies can be performed with the phantom by filling the compartments with selected fluids from the reservoirs, disconnecting the reservoirs and placing the phantom in the system bore. The phantom can be reused in other studies by replacing the fluids with different fluids.

8 Claims, 5 Drawing Sheets

SELECTIVELY ADJUSTABLE PHANTOM THAT IS COMPATIBLE WITH A MAGNETIC RESONANCE IMAGING SYSTEM AND ENVIRONMENT

BACKGROUND OF THE INVENTION

The field of the invention is nuclear magnetic resonance imaging (MRI) or spectroscopy (MRS) methods and systems. More particularly, the invention relates to a phantom that may be used to study the effectiveness of MRI and MRS methods and materials.

When a substance such as human tissue is subjected to a uniform magnetic field (polarizing field $B_0$), the individual magnetic moments of the spins in the tissue attempt to align with this polarizing field, but precess about it in random order at their characteristic Larmor frequency. If the substance, or tissue, is subjected to a magnetic field (excitation field $B_1$) which is in the x-y plane and which is near the Larmor frequency, the net aligned moment, Mz, may be rotated, or "tipped", into the x-y plane to produce a net transverse magnetic moment Mt. A signal is emitted by the excited spins after the excitation signal $B_1$ is terminated, this signal may be received and processed to form an image.

When utilizing these signals to produce images, magnetic field gradients ($G_x$, $G_y$ and $G_z$) are employed. Typically, the region to be imaged is scanned by a sequence of measurement cycles in which these gradients vary according to the particular localization method being used. The resulting set of received NMR signals are digitized and processed to reconstruct the image using one of many well known reconstruction techniques.

Phantoms are devices that are placed in the bore of an MRI system to test or calibrate its operation. Phantoms may be made of materials having known magnetic resonance properties or they may contain cavities filled with such materials. The MRI system is operated with the phantom in place to produce a spectrum or an image from which proper operation of the MRI system may be determined. The shape and size of the phantom or its cavities may be designed to measure magnetic field strength or field homogeneity and it may be used in combination with a procedure that enables calibration or trimming of such fields. Phantoms used in this manner are exemplified by those disclosed in U.S. Pat. No. 5,036,280; and published U.S. Pat. Appln. No. 2003/0086535.

Phantoms are also designed to model anatomical structures so that imaging or spectroscopy methods can be developed which accurately depict or represent such structures. As described in U.S. Pat. No. 6,205,871, for example, vascular structures are modeled with a phantom in order to test the efficacy of magnetic resonance angiography methods, and a phantom is disclosed in published U.S. Pat. Appln. No. 2006/0195030 that uses fiber bundles to create phantoms for use in testing diffusion tensor imaging (DTI) methods.

Manufacturing methods enable phantoms to be constructed with subresolvable regions. Three-dimensional fabrication methods such as printing on a thin film sheet or substrate using photo lithography, electrostatic xerographic printing or etching as disclosed in U.S. Pat. No. 6,720,766 may be used to produce cavities and fluid passages in the phantom that are smaller than the voxel size of a high resolution MR image. This technology is used in prior phantoms to model a specific anatomic structure or to achieve a specific effect.

SUMMARY OF THE INVENTION

The present invention is a phantom for use in testing MR methods and materials. More particularly, the phantom is constructed with a plurality of fluid circuits that each includes a reservoir for a fluid that may be forced into an array of compartments formed in the phantom. The compartments in each fluid circuit are preferably subresolvable in size and are located adjacent the subresolvable compartments in other fluid circuits.

A general object of the invention is to provide a phantom that can be used in many different MR studies. To study the effectiveness of a spectroscopy method, for example, fluids containing different metabolites may be employed in the different fluid circuits of the phantom to determine if the method will resolve the different metabolites in a voxel.

Another aspect of the invention is to separate the array of compartments into a plurality of sub-arrays in which the relative amount of fluids from the separate reservoirs differ in each sub-array. For example, in one sub-array the compartments are designed to contain 20% fluid from one reservoir and 80% fluid from another reservoir and in another sub-array the compartments contain 50% fluid from each reservoir. The MR signals from each sub-array of compartments will be affected by the ratio of fluids in each and this enables one to determine what ratio of fluids (such as metabolites or contrast agents) will have a discernable impact on the MR image or spectrum.

DESCRIPTION OF THE PREFERRED EMBODIMENT

Figure 1:
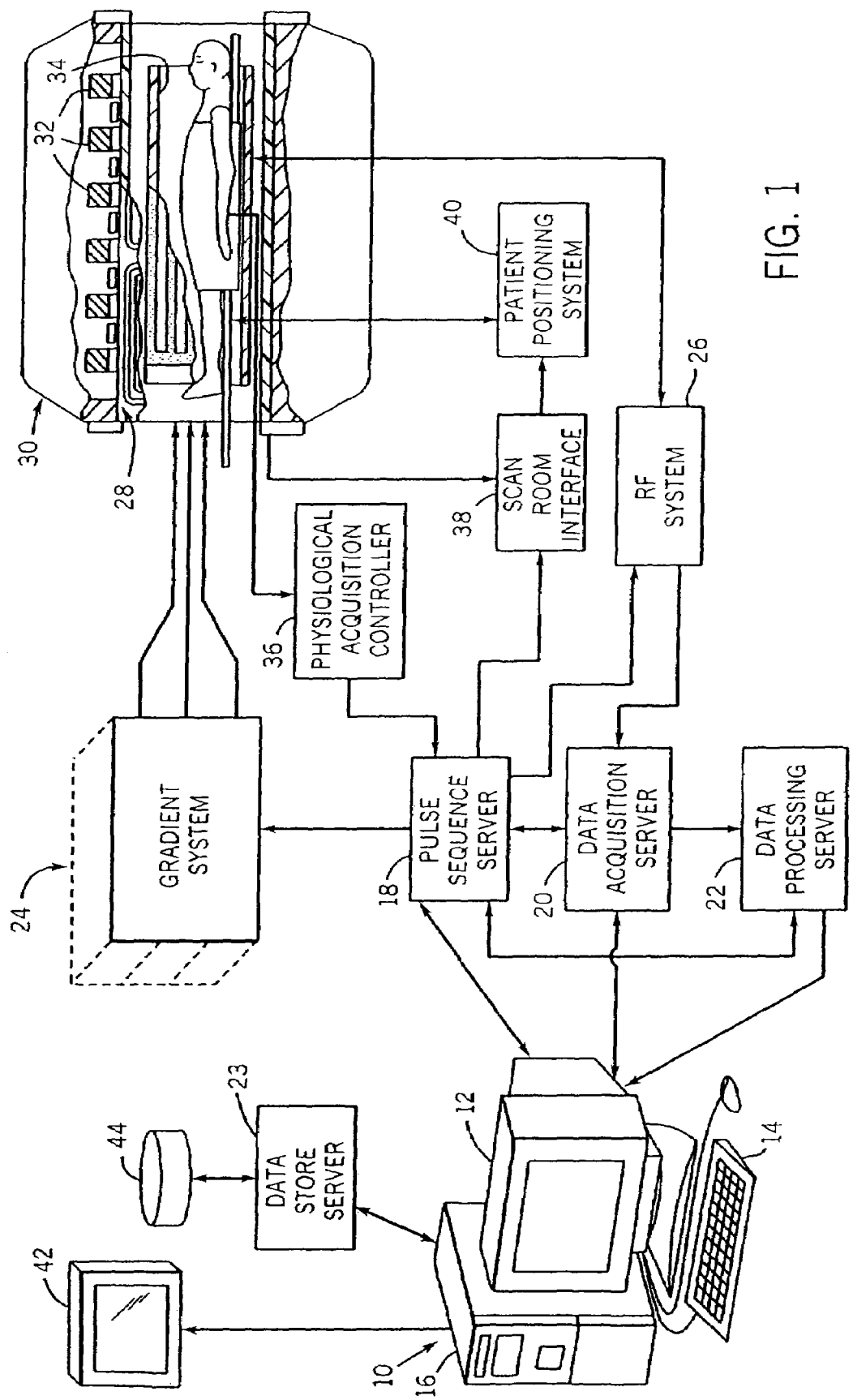
FIG. 1 is a block diagram of an MRI system which employs the present invention.

Referring particularly to FIG. 1, the preferred embodiment of the invention is employed in an MRI system. The MRI system includes a workstation 10 having a display 12 and a keyboard 14. The workstation 10 includes a processor 16 which is a commercially available programmable machine running a commercially available operating system. The workstation 10 provides the operator interface which enables scan prescriptions to be entered into the MRI system.

The workstation 10 is coupled to four servers: a pulse sequence server 18; a data acquisition server 20; a data processing server 22, and a data store server 23. In the preferred embodiment the data store server 23 is performed by the workstation processor 16 and associated disc drive interface circuitry. The server 18 is performed by a separate processor and the servers 20 and 22 are combined in a single processor. The workstation 10 and each processor for the servers 18, 20 and 22 are connected to an Ethernet communications network. This network conveys data that is downloaded to the servers 18, 20 and 22 from the workstation 10, and it conveys data that is communicated between the servers.

The pulse sequence server 18 functions in response to instructions downloaded from the workstation 10 to operate a gradient system 24 and an RF system 26. Gradient waveforms necessary to perform the prescribed scan are produced and applied to the gradient system 24 which excites gradient coils in an assembly 28 to produce the magnetic field gradients $G_x$, $G_y$, and $G_z$ used for position encoding NMR signals. The gradient coil assembly 28 forms part of a magnet assembly 30 which includes a polarizing magnet 32 and a whole-body RF coil 34.

RF excitation waveforms are applied to the RF coil 34 by the RF system 26 to perform the prescribed magnetic resonance pulse sequence. Responsive NMR signals detected by the RF coil 34 are received by the RF system 26, amplified, demodulated, filtered and digitized under direction of commands produced by the pulse sequence server 18. The RF system 26 includes an RF transmitter for producing a wide variety of RF pulses used in MR pulse sequences. The RF transmitter is responsive to the scan prescription and direction from the pulse sequence server 18 to produce RF pulses of the desired frequency, phase and pulse amplitude waveform. The generated RF pulses may be applied to the whole body RF coil 34 or to one or more local coils or coil arrays.

The RF system 26 also includes one or more RF receiver channels. Each RF receiver channel includes an RF amplifier that amplifies the NMR signal received by the coil to which it is connected and a quadrature detector which detects and digitizes the I and Q quadrature components of the received NMR signal. The magnitude of the received NMR signal may thus be determined at any sampled point by the square root of the sum of the squares of the I and Q components:

$$M=\sqrt{I^2+Q^2},$$

and the phase of the received NMR signal may also be determined:

$$\phi=\tan^{-1}Q/I.$$

The pulse sequence server 18 also optionally receives patient data from a physiological acquisition controller 36. The controller 36 receives signals from a number of different sensors connected to the patient, such as ECG signals from electrodes or respiratory signals from a bellows. Such signals are typically used by the pulse sequence server 18 to synchronize, or "gate", the performance of the scan with the subject's respiration or heart beat.

The pulse sequence server 18 also connects to a scan room interface circuit 38 which receives signals from various sensors associated with the condition of the patient and the magnet system. It is also through the scan room interface circuit 38 that a patient positioning system 40 receives commands to move the patient to desired positions during the scan.

The digitized NMR signal samples produced by the RF system 26 are received by the data acquisition server 20. The data acquisition server 20 operates in response to instructions downloaded from the workstation 10 to receive the real-time NMR data and provide buffer storage such that no data is lost by data overrun. In some scans the data acquisition server 20 does little more than pass the acquired NMR data to the data processor server 22. However, in scans which require information derived from acquired NMR data to control the further performance of the scan, the data acquisition server 20 is programmed to produce such information and convey it to the pulse sequence server 18. For example, during prescans NMR data is acquired and used to calibrate the pulse sequence performed by the pulse sequence server 18. Also, navigator signals may be acquired during a scan and used to adjust RF or gradient system operating parameters or to control the view order in which k-space is sampled. And, the data acquisition server 20 may be employed to process NMR signals used to detect the arrival of contrast agent in an MRA scan. In all these examples the data acquisition server 20 acquires NMR data and processes it in real-time to produce information which is used to control the scan.

The data processing server 22 receives NMR data from the data acquisition server 20 and processes it in accordance with instructions downloaded from the workstation 10. Such processing may include, for example: Fourier transformation of raw k-space NMR data to produce two or three-dimensional images; the application of filters to a reconstructed image; the performance of a back projection image reconstruction of acquired NMR data; the calculation of functional MR images; the calculation of motion or flow images, etc.

Images reconstructed by the data processing server 22 are conveyed back to the workstation 10 where they are stored. Real-time images are stored in a data base memory cache (not shown) from which they may be output to operator display 12 or a display 42 which is located near the magnet assembly 30 for use by attending physicians. Batch mode images or selected real time images are stored in a host database on disc storage 44. When such images have been reconstructed and transferred to storage, the data processing server 22 notifies the data store server 23 on the workstation 10. The workstation 10 may be used by an operator to archive the images, produce films, or send the images via a network to other facilities.

Figure 2:
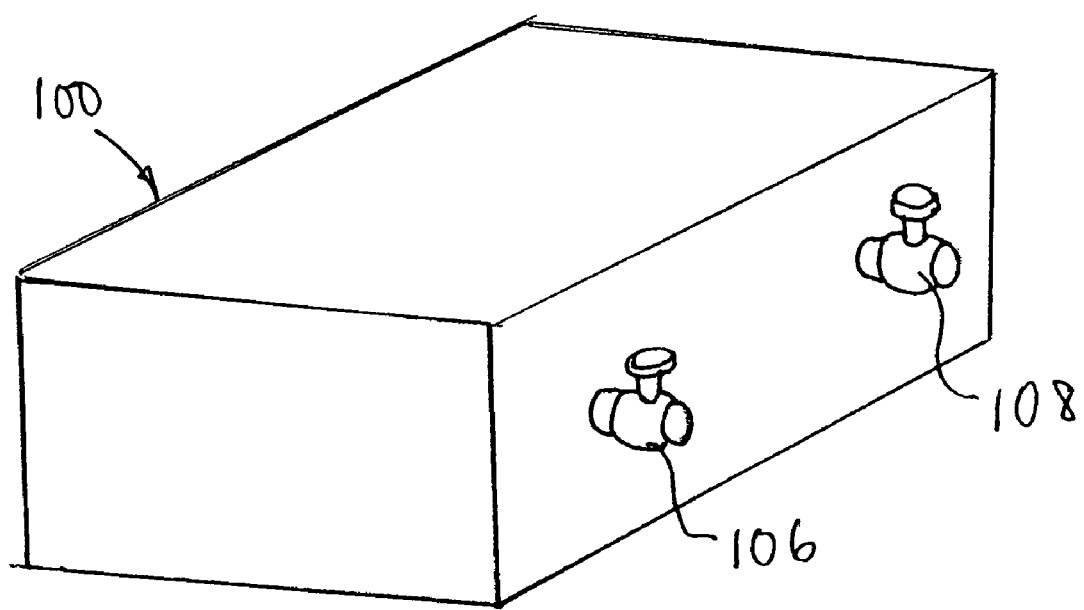
FIG. 2 is a pictorial view of a preferred embodiment of a phantom constructed according to the present invention.

The phantom constructed according to the teachings of the present invention is inserted into the bore of the magnet in place of the human subject shown in FIG. 1. A preferred embodiment of the phantom is shown in FIGS. 2-4, where the phantom housing 100 in FIG. 2 is the element actually placed into the MRI system.

Figure 3:
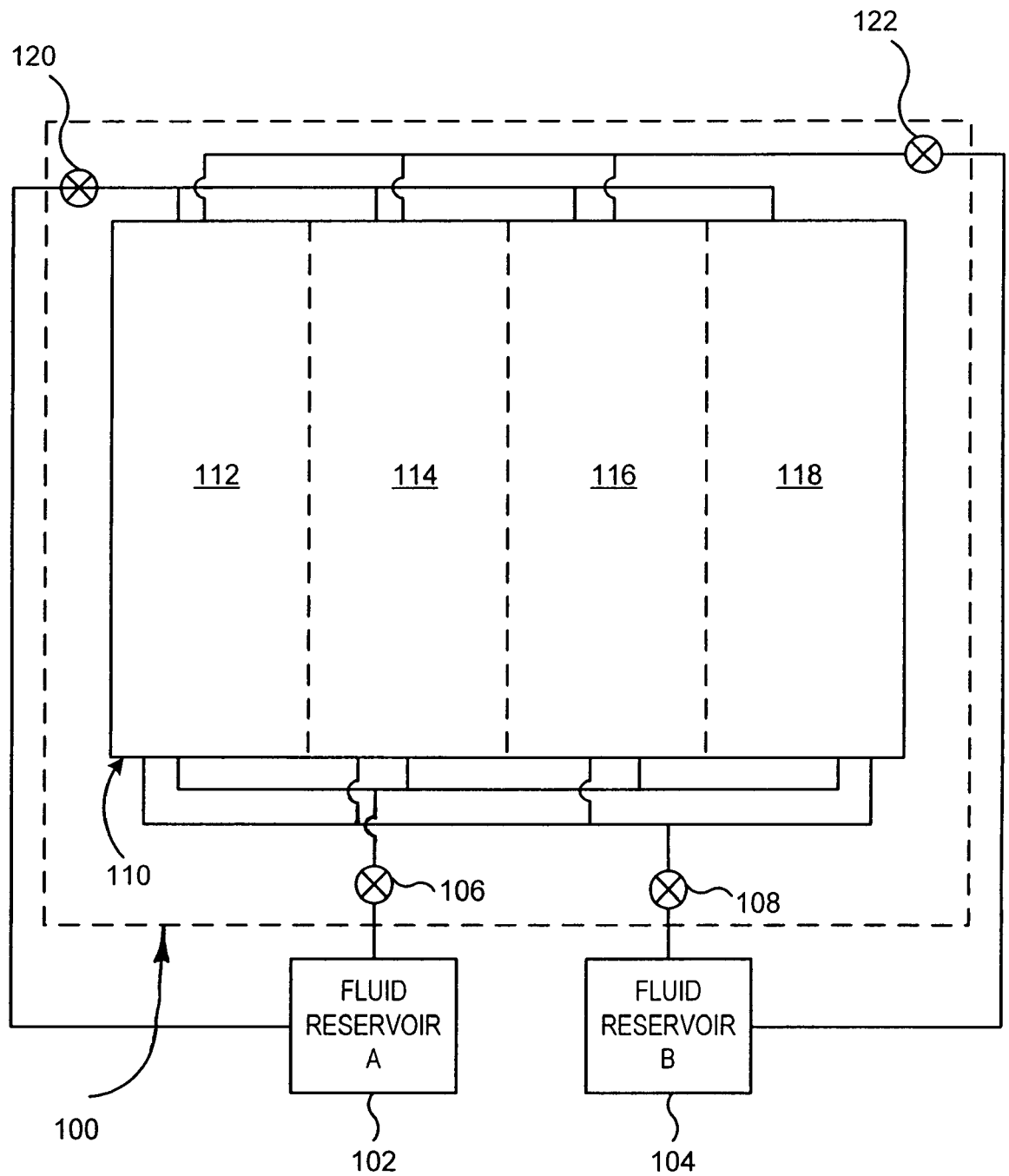
FIG. 3 is a schematic diagram of the phantom in FIG. 2 attached to two fluid reservoirs.

Referring particularly to FIG. 3, the phantom includes two fluid reservoirs 102 and 104 that store fluids such as contrast agents and metabolites that are to be used in a phantom study. Each fluid reservoir 102 and 104 is connected to fluid circuits in the phantom housing 100 through respective valves 106 and 108. Each fluid circuit includes an array of compartments in the housing 100 which are filled with fluid from the reservoir 102 or 104 to which they connect. The array of compartments indicated schematically in FIG. 3 at 110 is in turn divided into sub-arrays 112, 114, 116 and 118, and as will be described below, each subarray provides a different mix of the reservoir fluids. The fluid circuits convey fluid from the reservoirs 102 and 104 into selected compartments in the array 110 and the over flow fluid from reservoir 102 exits the array 110 through a valve 120 and is recirculated back to reservoir 102. Similarly, over flow fluid from reservoir 104 exits the array 100 through a valve 122 and is recirculated back to the reservoir 104.

The phantom is prepared for a study by filling the reservoirs 102 and 104 with the fluids to be used, and these fluids are pumped through the compartment array 110. When all the compartments are filled with fluid, the valves 106, 108 and 120, 122 are closed and disconnected from the reservoirs 102 and 104. The phantom housing 100 with enclosed compartment array 110 is then placed in the bore of the MRI system and a test procedure is run. When the test procedure is finished the phantom housing 100 is removed from the bore and the valves 106, 108, 120 and 122 are opened to drain the fluids from the compartment array 110. The phantom can then be reused in an entirely different test procedure by filling the reservoirs with different fluids.

Figure 4:
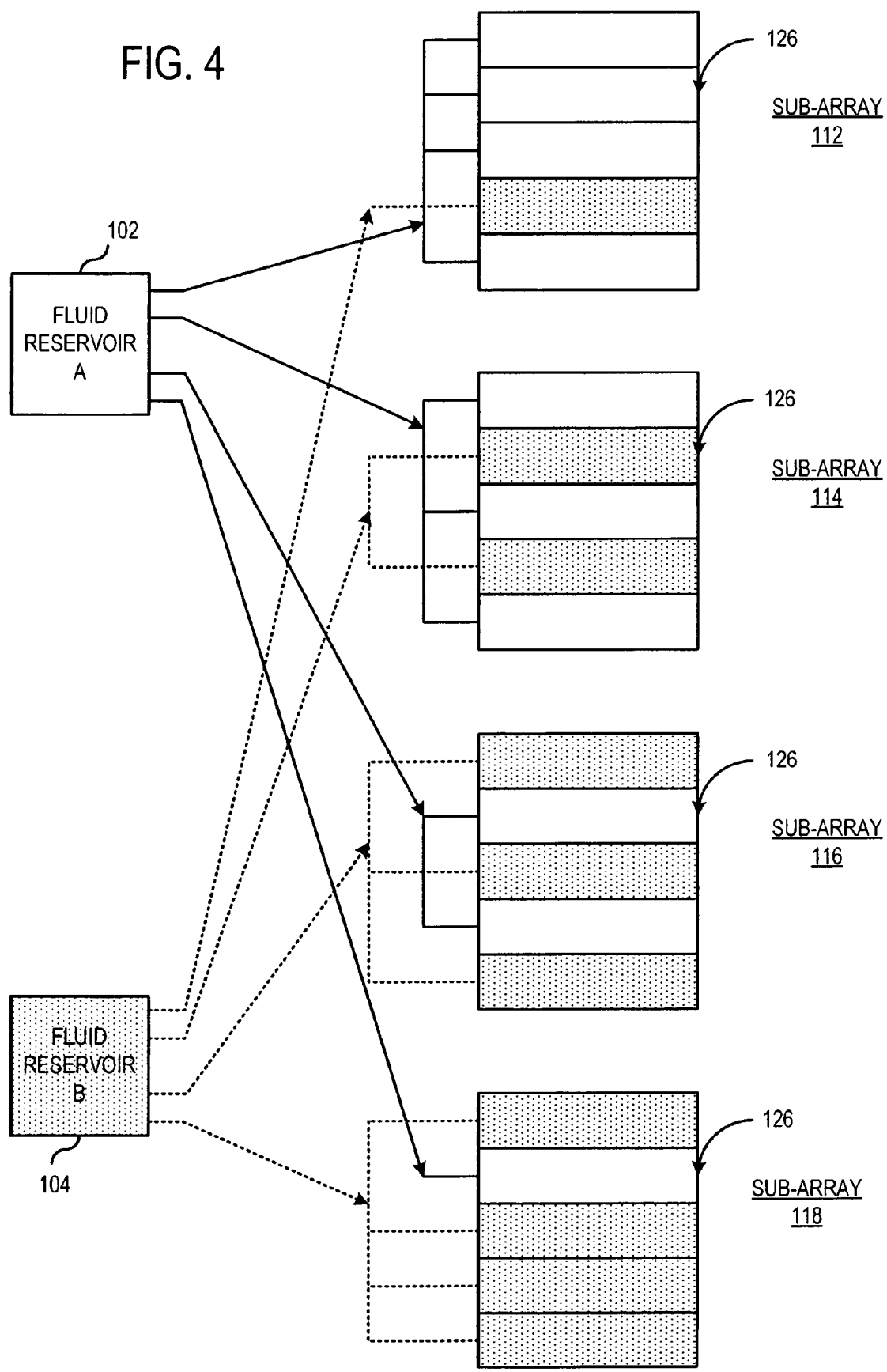
FIG. 4 is a schematic diagram showing the connection of compartments in the phantom to the fluid reservoirs.

Referring particularly to FIGS. 3 and 4, the compartment array 110 is constructed using a three-dimensional fabrication method that enables each compartment to be formed at a subresolvable size. The choice of fabrication method is mainly dependent on the desired structural resolution, as well as the ability to make distinct compartments. The compartment array 110 is organized as 1 mm cubes 126 disposed along three Cartesian axes to fill a rectangular space. Each cube 126 contains five compartments that receive fluid from either of reservoir 102 or 104.

The cubes 126 in each sub-array 112,114,116 and 118 are distinguished from each other by the fluid which fills each of its five compartments. Referring to FIG. 4, the cubes 126 in the sub-array 112 have four compartments connected to reservoir 102 and only one compartment connected to reservoir 104. As a result, an MR image or spectrum will "see" each voxel sized cube 126 in sub-array 112 as 80% fluid A and 20% fluid B.

The cubes 126 in the other sub-arrays 114,116 and 118 contain a different mix of fluids A and B. Sub-array 114 contains cubes 126 in which three compartments receive fluid A and two compartments receive fluid B. The cubes 126 in sub-array 116 have two compartments receiving fluid A and three compartments receiving fluid B, and cubes 126 in sub-array 118 have one compartment receiving fluid A and four compartments receiving fluid B. As a result, the preferred embodiment of the invention enables four different mixes of the two fluids A and B at a subresolvable scale.

It should be apparent to those skilled in the art that many variations are possible from the above-described preferred embodiment. The number of compartments in each subresolvable cube 126 can be increased to enable a more highly resolved range of fluid A and B mixes. Also, the compartment array 110 need not be formed as cubical shaped collections of compartments, but instead may be shaped to model specific tissues or anatomic structures.

While two fluid reservoirs and corresponding fluid circuits are employed in the preferred embodiment, additional fluid reservoirs and associated fluid circuits may be employed. In such case each cube 126 will contain compartments that are selectively connected to the additional fluid reservoirs and the range of fluid mixes will take on additional dimensions.

An example use of the preferred phantom is to fill the two reservoirs with solutions containing chemicals with nearly overlapping resonances. By acquiring MRS measurements on compartments containing different mixes of the two solutions, it can then be determined at which mixture the MRS measurement method can distinguish between the two metabolites.

While the preferred embodiment is a phantom for MRI studies, the same design principles may be applied for other modalities where a sub-resolution mixture of circuits containing liquids or gas can provide the signal sources. Examples of such other modalities include radionuclide imaging (where the different reservoirs are filled with fluids containing different radionuclide sources) and optical tomography (where the different reservoirs are filled with fluids having different optical properties).

Figure 5:
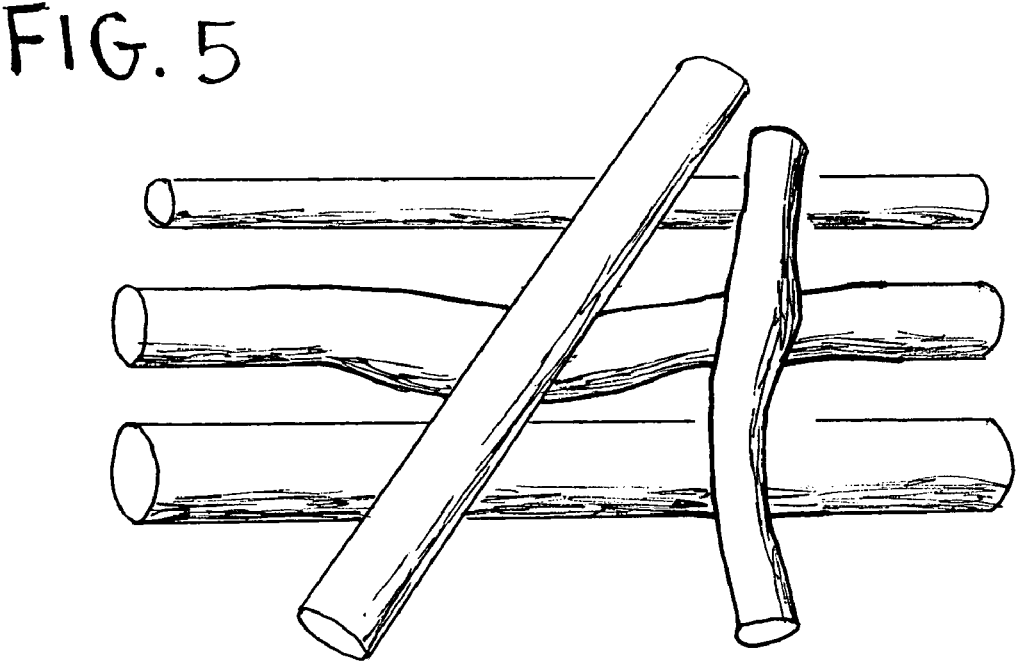
FIG. 5 is a pictorial view of a compartment structure in a first alternative embodiment of the invention.

A second preferred embodiment of the phantom is constructed to mimic the diffusion properties of tissue or other homogeneous media. The circuits in this embodiment include numerous tube-like structures such as those indicated in FIG. 5 that produce a directional asymmetry in the diffusion of the material contained in the circuit. An individual tube-like structure can have a variety of properties such as diameter, curvature and direction that can vary between neighboring structures as well as varying along its length.

Figure 6:
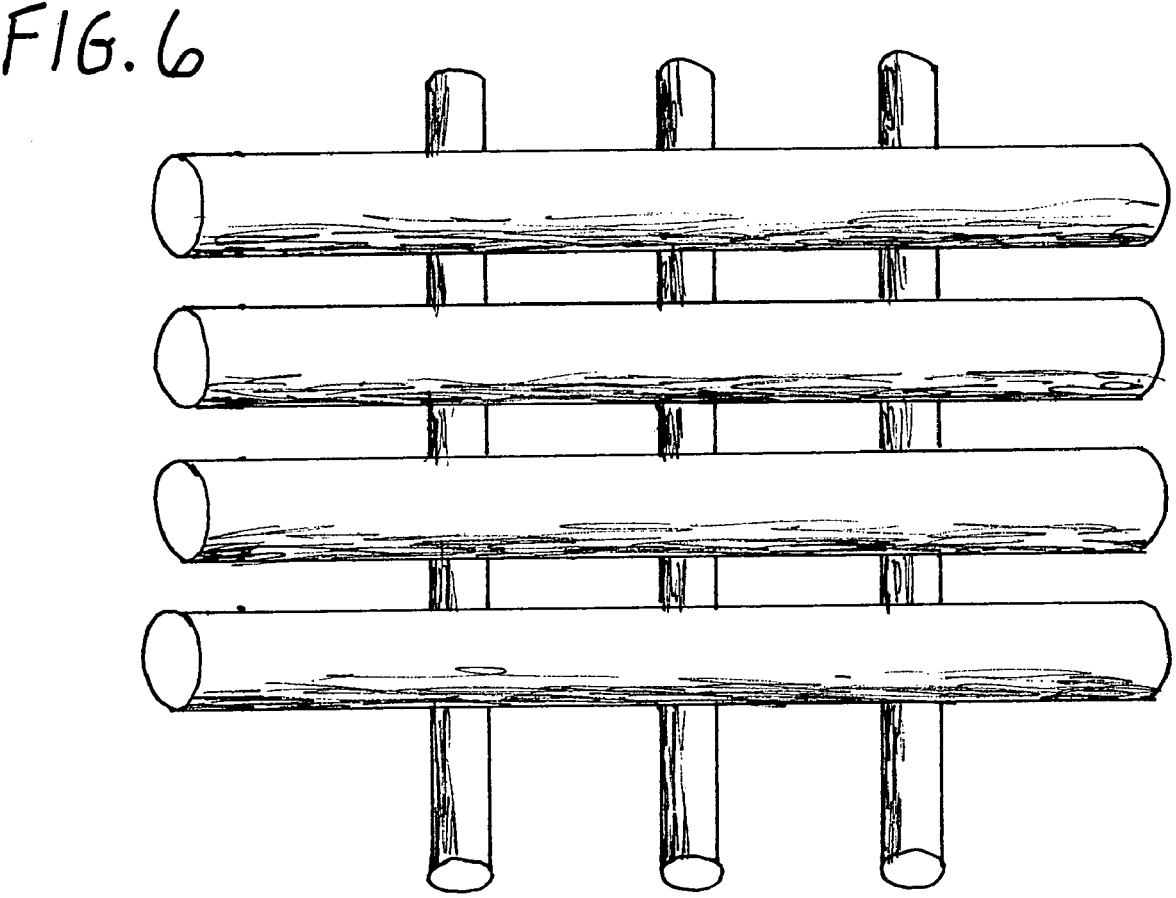
FIG. 6 is a pictorial view of a compartment structure in a second alternative embodiment of the invention.

A third preferred embodiment is a phantom whose electrical conductivity is spatially anisotropic. The circuits are filled with a conductive medium, such as saline. By constructing the circuits as shown in FIG. 6 with fluid passages of different diameters in different directions, greater conductivity in certain directions is achieved and an isotopic conductivity can be created.

The invention claimed is:

1. A selectively adjustable phantom system configured for use in a medical imaging system that is compatible with a magnetic resonance imaging environment, the selectively adjustable phantom system comprising:

A phantom housing having formed therein an array of compartments divided into sub-arrays that are distinguished from each other by a ratio of the amount of fluid resent within the compartments;

a plurality of fluid circuits, each fluid circuit connected to at least one of said compartments in a sub-array;

a plurality of detachable fluid reservoirs external to the phantom housing and selectively coupled through the plurality of fluid circuits into portions of the sub-arrays within the phantom housing; and a control system configured to allow user selection of the selectively coupled portions of the subarrays connecting with the plurality of detachable fluid reservoirs in order to allow the sub-arrays to be selectively filled to a desired level through the fluid circuits by the fluid reservoirs.

2. The selectively adjustable phantom recited in claim 1 in which each fluid reservoir contains a fluid comprised of various metabolites.

3. The selectively adjustable phantom as recited in claim 1 in which each sub-array has a subresolvable size with respect to the medical imaging system in which it is used.

4. The selectively adjustable phantom as recited in claim 3 in which the sub-arrays are arranged in a three-dimensional configuration within the phantom housing.

5. The selectively adjustable phantom as recited in claim 1 in which the compartments in each sub-array are contiguous to one another.

6. The selectively adjustable phantom as recited in claim 1 in which the medical imaging system is a magnetic resonance spectroscopy system and the reservoirs are filled with fluids having different resonance responses.

7. The selectively adjustable phantom as recited in claim 1 in which fluids within the compartments in the sub-arrays are selectively recirculated back into the fluid reservoirs.

8. The selectively adjustable phantom as recited in claim 7 in which the selected amount of fluids from the separate fluid reservoirs differ in each sub-array.

* * * * *